(12) United States Patent
Benchikh et al.

(10) Patent No.: US 9,952,206 B2
(45) Date of Patent: Apr. 24, 2018

(54) IMMUNOASSAY FOR DETECTING KRATOM, ITS CONSTITUENTS AND THEIR USE

(71) Applicant: Randox Laboratories Limited, Crumlin, Antrim (GB)

(72) Inventors: Elouard Benchikh, Crumlin (GB); Ivan McConnell, Crumlin (GB); Philip Lowry, Crumlin (GB); Peter Fitzgerald, Crumlin (GB)

(73) Assignee: Randox Laboratories Limited, Crumlin, Antrim (IE)

( * ) Notice: Subject to any disclaimer, the term of this patent is extended or adjusted under 35 U.S.C. 154(b) by 458 days.

(21) Appl. No.: 14/184,422

(22) Filed: Feb. 19, 2014

(65) Prior Publication Data

US 2014/0242617 A1    Aug. 28, 2014

(30) Foreign Application Priority Data

Feb. 22, 2013 (GB) .................................. 1303168.7

(51) Int. Cl.
*G01N 33/53* (2006.01)
*C07K 16/16* (2006.01)
*C07K 16/44* (2006.01)

(52) U.S. Cl.
CPC ......... *G01N 33/5308* (2013.01); *C07K 16/16* (2013.01); *C07K 16/44* (2013.01); *C07K 2317/33* (2013.01)

(58) Field of Classification Search
CPC .... C07K 16/16; C07K 16/44; C07K 2317/33; G01N 33/5308
See application file for complete search history.

(56) References Cited

U.S. PATENT DOCUMENTS

2010/0291600 A1* 11/2010 Fitzgerald ............. C07K 16/16
435/7.92

FOREIGN PATENT DOCUMENTS

WO    WO 2013/147586 A1 *  3/2013

OTHER PUBLICATIONS

Szurdoki et al., "Important Factors in Hapten Design and Enzyme-Linked Immunosorbent Assay Development," in Immunoanalysis of Agrochemicals; Nelson, J., et al.; ACS Symposium Series, 1995, vol. 586, Chapter 4, pp. 39-63.*
Peterson et al., "Using hapten design to discover therapeutic monoclonal antibodies for treating methamphetamine abuse," J. Pharmacol. Exp. Ther., Jul. 2007; vol. 322, No. 1, pp. 30-39. Epub Apr. 23, 2007.*
Pravetoni et al., "Structurally distinct nicotine immunogens elicit antibodies with non-overlapping specificities," Biochem. Pharmacol., Feb. 15, 2012; vol. 83, No. 4, pp. 543-550, Published online Nov. 15, 2011.*
Richard A. Goldsby, "Immunology," Macmillan, Nov. 29, 2002, p. 69.*
Scott-Moncrief et al., "Evaluation of antithyroglobulin antibodies after routine vaccination in pat and research dogs," J. Am. Vet. Med., 2002, vol. 221, No. 4, p. 499.*
Janchawee et al., "A high-performance liquid chromatographic method for determination of mitragynine in serum and its application to a pharmacokinetic study in rats," *Biomedical Chromatography* 21:176-183 (2007).
Kaewklum et al., "Detection of mitragynine and it metabolite on urine following ingestion of leaves of *Mitragyna speciosa* korth," *Recent Advances in Doping Analysis* 13:403-406 (2005).
Le et al., "Analysis of mitragynine and metabolites in human urine for detecting the use of the psychoactive plant kratom," *Journal of Analytical Toxicology* 36:616-625 (2012).

* cited by examiner

*Primary Examiner* — Galina Yakovleva
(74) *Attorney, Agent, or Firm* — Klarquist Sparkman, LLP (57) ABSTRACT

The invention relates to the field of drug detection and describes antibody-based components methods and kits for the detection and quantification of alkaloids of the plant kratom. The invention is underpinned by novel antibodies which specifically bind to mitragynine alkaloids found in the kratom plant and their metabolites.

8 Claims, 5 Drawing Sheets

IMMUNOASSAY FOR DETECTING KRATOM, ITS CONSTITUENTS AND THEIR USE

CROSS REFERENCE TO RELATED APPLICATIONS

This application claims priority under 35 U.S.C. § 119 to United Kingdom Application No 1303168.7 filed Feb. 22, 2013, which is incorporated by reference in its entirety.

BACKGROUND TO THE INVENTION

The invention relates to the field of drug analytics and the detection and quantification of the main constituent of *Mitragyna speciosa*, commonly referred to as 'Kratom', mitragynine (systematic name: (E)-2-[(2S,3S,12bS)-3-ethyl-8-methoxy-1,2,3,4,6,7,12,12b-octahydroindolo[2,3-a]quinozilizin-2-yl]-3-methoxy propenoic acid methyl ester) and its principle metabolite 8-desmethylmitragynine (systematic name: (E)-2-[(2S,3S,12bS)-3-ethyl-8-hydroxy-1,2,3,4,6,7,12,12b-octahydroindolo[2,3-a]quinozilizin-2-yl]-3-methoxy propenoic acid methyl ester—also referred to in the literature as 5-desmethylmitragynine and 9-desmethylmitragynine). The recent increase in recreational drug-induced psychostimulation, and the concomitant variety and number of substances ingested to achieve this effect, includes the use of kratom. Kratom is purported to have medicinal properties and, although illegal in certain countries, it remains legal in the US, UK, and most of Europe. There have been recent reports of numerous fatalities associated with its ingestion and there is increasing interest in kratom detection, by way of mitragynine and its metabolites, for toxicological and research purposes. Described analytical methods for detection and quantification of mitragynine and metabolites use the relatively expensive, specialist operator-dependent techniques of high performance liquid chromatography (HPLC) or mass-spectroscopy linked to either gas chromatography (GC-MS) or liquid chromatography (LC-MS) (e.g. Kaewklum, 2005; Janchawee, 2007; Le, 2012). The techniques can be further complicated by requiring a sample pre-treatment prior to analysis. Thus, there is a clinical and forensic need to rapidly and economically detect and quantify mitragynine and its metabolites in patient samples and substances suspected of incorporating kratom.

REFERENCES

Janchawee et al., 2007. A high-performance liquid chromatographic method for determination of mitragynine in serum and its application to a pharmacokinetic study in rates. Biomedical Chromatography, 21: 176-83.

Kaewklum S. et al., 2005. Detection of mitragynine and its metabolite in urine following ingestion of leaves of *Mitragyna speciosa* korth. In: Recent advances in doping analysis (13) pp 403-406. W. Schanzer, H. Geyer, A. Gotzmann, U. Mareck (eds.), Sport and Buch Strauβ, Köln.

Le D. et al., 2012. Analysis of mitragynine and metabolites in human urine for detecting the use of the psychoactive plant kratom. Journal of Analytical Toxicology, 36: 616-625.

SUMMARY OF INVENTION

Immunodiagnostics is a relatively inexpensive and readily implemented analytical technology. The invention described herein, underpinned by an antibody which binds mitragynine and 8-desmethylmitragynine, overcomes the problems associated with current kratom analytical techniques. The invention also describes methods, an immunoassay and substrates incorporating the antibody.

According to a first aspect of the present invention, there is provided an antibody capable of binding, optionally specifically binding, to at least one epitope of mitragynine and/or its respective metabolite.

Optionally, the antibody is capable of binding, optionally specifically binding, to at least one epitope of mitragynine and its respective metabolite.

Optionally, the mitragynine metabolite comprises modification by a carboxylic acid or a sulphonic acid. Still further optionally, the mitragynine metabolite comprises modification by a glucuronic acid or a sulphuric acid.

Optionally, the mitragynine metabolite comprises a modification at the 8-position.

Optionally, the mitragynine metabolite comprises addition of a carboxylic acid or a sulphonic acid. Still further optionally, the mitragynine metabolite comprises addition of a glucuronic acid or a sulphuric acid. Optionally, the mitragynine metabolite comprises addition at the 8-position of a carboxylic acid or a sulphonic acid. Still further optionally, the mitragynine metabolite comprises addition at the 8-position of a glucuronic acid or a sulphuric acid.

Optionally, the mitragynine metabolite is selected from 8-glucuronidyldmitragynine and 8-sulphonyldmitragynine.

Optionally, the mitragynine metabolite comprises substitution at the 8-position of an alkyl group by a hydrogen atom. Further optionally, the mitragynine metabolite comprises substitution at the 8-position of a methyl group by a hydrogen. Still further optionally, the mitragynine metabolite is 8-desmethylmitragynine.

Optionally, the antibody is capable of binding, optionally specifically binding, to at least one epitope of mitragynine and 8-desmethylmitragynine.

Optionally, the antibody is capable of specifically binding to mitragynine and cross-reacts with 8-desmethylmitragynine.

Optionally, the antibody has a cross-reactivity to 8-desmethylmitragynine of at least 10%, optionally at least 30%, further optionally at least 50% relative to mitragynine. Further optionally, the antibody has a cross-reactivity to 8-desmethylmitragynine of at least 10%, optionally at least 30%, further optionally at least 50% relative to mitragynine, when mitragynine has a cross-reactivity of 100%.

Optionally, the antibody is capable of binding, optionally specifically binding, to at least one epitope of one or more of speciogynine, speciociliatine, paynantherine, and/or their respective metabolites.

Optionally, the antibody is selected from a polyclonal antibody, a monoclonal antibody, a humanised antibody, a chimeric antibody, and a short-chain or single chain variable fragment or fragments.

Optionally, the antibody is selected from a polyclonal antibody, and a monoclonal antibody.

According to a second aspect of the present invention, there is provided an antibody derivable, optionally derived, from an immunogen having the general structure (0):

(0)

[Structure 0 diagram]

wherein
W is selected from N, O, and S;
X is -Q-Z—, wherein
Z is a crosslinking group selected from a $C_1$-$C_{10}$, optionally a $C_1$-$C_5$, substituted or unsubstituted, straight or branched chain, saturated or unsaturated alkyl moiety; and
Q is selected from a carboxylic acid or an ester thereof, an aldehyde, an amino group, a maleimide, a halocarboxylic acid or an ester thereof, a dithiopyridyl moiety, a vinylsulphone moiety, and a thiocarboxylic acid or an ester thereof; and
Y is an antigenicity conferring carrier material.

Optionally, W is attached to any one of the 8-position, 9-position, 10-position, and 11-position of the fused heterocyclic ring of Structure (0). Further optionally, W is attached to the 8-position of the fused heterocyclic ring of Structure (0).

Optionally, W is O. Further optionally, W is O and is attached to the 8-position of the fused heterocyclic ring of Structure (0).

Optionally, Z is attached to W.

Optionally, Z is a $C_1$-$C_{10}$, substituted or unsubstituted, straight or branched chain, saturated or unsaturated alkyl moiety. Further optionally, Z is a $C_1$-$C_5$, substituted or unsubstituted, straight or branched chain, saturated or unsaturated alkyl moiety. Still further optionally, Z is a $C_3$, substituted or unsubstituted, straight or branched chain, saturated or unsaturated alkyl moiety.

Optionally, Z is a substituted $C_3$ alkyl moiety. Further optionally, Z is a $C_3$ alkyl moiety substituted with an O. Still further optionally, Z is propanal.

Optionally, Q is attached to Z.
Optionally, Q is a carboxylic acid or an ester thereof.
Optionally, Y is attached to Q.
Optionally, Y is selected from polypeptides, proteins, and protein fragments Further optionally, Y is selected from bovine serum albumin, egg ovalbumin, bovine gamma globulin, bovine thyroglobulin, and keyhole limpet haemocyanin. Alternatively, Y is selected from synthetic poly(amino acids) having a sufficient number of available amino groups, such as lysine, or suitably reactive functional groups. Further alternatively, Y is selected from carbohydrates, yeasts, and polysaccharides.

Optionally, Y selected from keyhole limpet haemocyanin (KLH), bovine serum albumin (BSA), and bovine thyroglobulin (BTG). Further optionally, Y is an antigenicity conferring carrier material selected from bovine serum albumin (BSA), and bovine thyroglobulin (BTG).

Optionally, the immunogen has the general structure (0), wherein W is O; X is -Q-Z—, wherein Z is propanal (—$CH_2$—$CH_2$—CO—); and Q is carboxylic acid or an ester thereof; and Y is bovine thyroglobulin (BTG).

Optionally, the immunogen has the general structure (0), wherein W is O; X is -Q-Z—, wherein Z is propanal (—$CH_2$—$CH_2$—CO—); and Q is carboxylic acid or an ester thereof; and Y is bovine serum albumin (BSA).

Optionally, the immunogen has the general structure (I):

(I)

[Structure I diagram]

wherein
W is selected from N, O, and S;
X is -Q-Z—, wherein
Z is a crosslinking group selected from a $C_1$-$C_{10}$, optionally a $C_1$-$C_5$, substituted or unsubstituted, straight or branched chain, saturated or unsaturated alkyl moiety; and
Q is selected from a carboxylic acid or an ester thereof, an aldehyde, an amino group, a maleimide, a halocarboxylic acid or an ester thereof, a dithiopyridyl moiety, a vinylsulphone moiety, and a thiocarboxylic acid or an ester thereof; and
Y is an antigenicity conferring carrier material selected from keyhole limpet haemocyanin (KLH), bovine serum albumin (BSA), and bovine thyroglobulin (BTG).

Optionally, W is O. Further optionally, W is O and is attached to the 8-position of the fused heterocyclic ring of Structure (I).

Optionally, the immunogen has the general structure (II):

(II)

[Structure II diagram]

wherein
X is -Q-Z—, wherein
Z is a crosslinking group selected from a $C_1$-$C_{10}$, optionally a $C_1$-$C_5$, substituted or unsubstituted, straight or branched chain, saturated or unsaturated alkyl moiety; and
Q is selected from a carboxylic acid or an ester thereof, an aldehyde, an amino group, a maleimide, a halocarboxylic acid or an ester thereof, a dithiopyridyl moiety, a vinylsulphone moiety, and a thiocarboxylic acid or an ester thereof; and Y is an antigenicity conferring carrier material selected from keyhole limpet haemocyanin (KLH), bovine serum albumin (BSA), and bovine thyroglobulin (BTG).

According to a third aspect of the present invention, there is provided an assay comprising an antibody according to the present invention immobilised to a solid support.

Optionally, the solid support is selected from plastic or magnetic beads, polystyrene microtitre plates (ELISA plates), planar nitrocellulose, a ceramic biochip, and a biochip such as a plastic or glass.

According to a fourth aspect of the present invention, there is provided a kit comprising at least one antibody of the present invention, a conjugate, a calibrator, and instructions for use.

According to a fifth aspect of the present invention, there is provided a method of detecting or quantifying mitragynine and its respective metabolite, the method comprising the steps of contacting a sample with at least one antibody of the present invention; and deducing the presence or amount of mitragynine and its respective metabolite in the sample.

Optionally, the method further comprises the step of contacting the sample and the antibody with a conjugate.

Optionally, the method further comprises detecting the bound conjugate.

Optionally, the method comprises the steps of contacting a sample with at least one antibody of the present invention and a conjugate; detecting the bound conjugate; and deducing the presence or amount of mitragynine and its respective metabolite in the sample.

Optionally, the method is a method of detecting or quantifying mitragynine and its respective metabolite.

Optionally, the method is an in vitro method.

Optionally, the sample is an in vitro sample taken from an individual. Further optionally, the sample is a biological sample, optionally selected from hair, whole blood, serum, plasma, and urine.

Optionally, the conjugate has the general structure (III):

(III)

wherein X is an organic spacing group; and Y is a detectable labelling agent.

Optionally, X is -Q-Z—, wherein

Z is a crosslinking group selected from a $C_1$-$C_{10}$, optionally a $C_1$-$C_5$, substituted or unsubstituted, straight or branched chain, saturated or unsaturated alkyl moiety; and Q is selected from a carboxylic acid or an ester thereof, an aldehyde, an amino group, a maleimide, a halocarboxylic acid or an ester thereof, a dithiopyridyl moiety, a vinylsulphone moiety, and a thiocarboxylic acid or an ester thereof.

Optionally, Z is attached to O.

Optionally, X is -Q-Z—, wherein Z is a $C_1$-$C_6$, substituted or unsubstituted, straight or branched chain, saturated or unsaturated alkyl moiety; and Q is a carboxylic acid or an ester thereof. Alternatively, X is -Q-Z—, wherein Z is a $C_1$-$C_5$, substituted or unsubstituted, straight or branched chain, saturated or unsaturated alkyl moiety; and Q is an amino group.

Optionally, X is -Q-Z—, wherein Z is a $C_6$, substituted with two O; and Q is a carboxylic acid or an ester thereof.

Optionally, X is -Q-Z—, wherein Z is a $C_1$-$C_5$ alkyl moiety substituted with an O; and Q is an amino group.

Optionally, Y is attached to Q.

Optionally, Y is selected from an enzyme, a luminescent substance, a radioactive substance, and a mixture thereof.

Optionally, Y is an enzyme, optionally a peroxidase, further optionally horseradish peroxidase (HRP).

Optionally, the luminescent substance is selected from a bioluminescent, chemiluminescent, and fluorescent material.

BRIEF DESCRIPTION OF THE FIGURES

FIG. 4—8-desmethylmitragynine hemisuccinate (Hapten-3, Top) and Hapten-3 HRP conjugate (bottom).

DETAILED DESCRIPTION OF THE INVENTION

Figure 1:
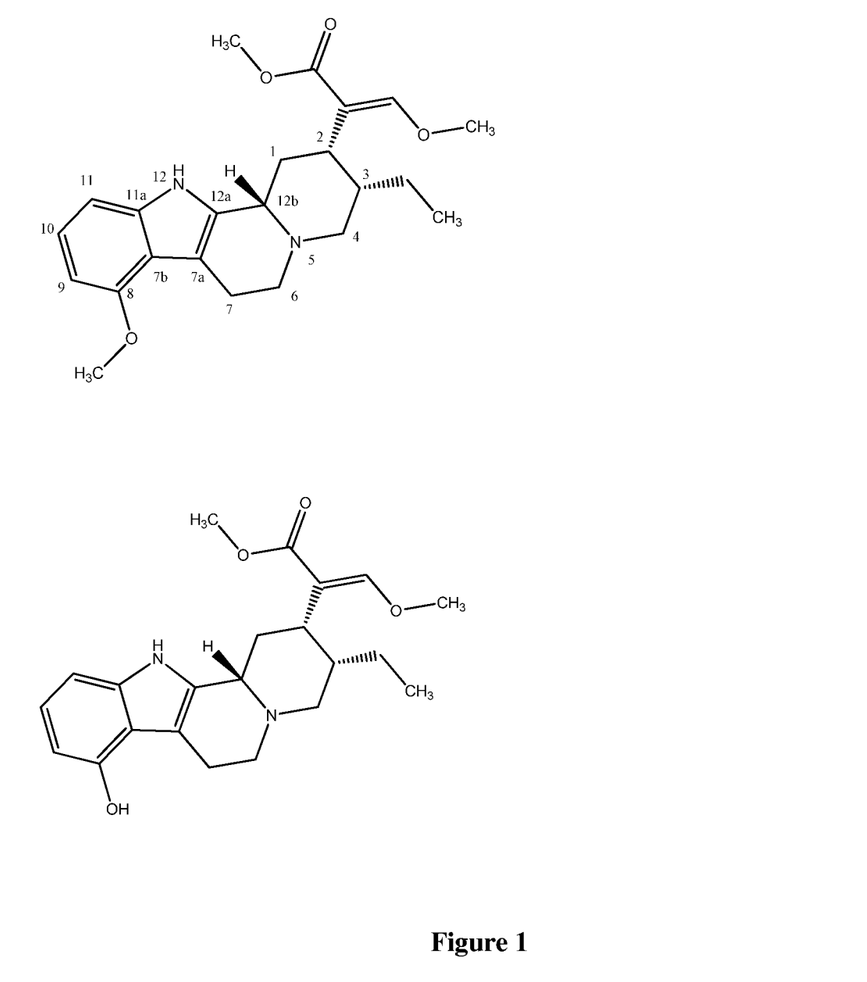
FIG. 1—Kratom alkaloids and identified metabolites. Numbering highlighted on mitragynine is adopted throughout. Mitragynine with numbering (top), and 8-desmethylmitragynine (bottom).
Figure 2:
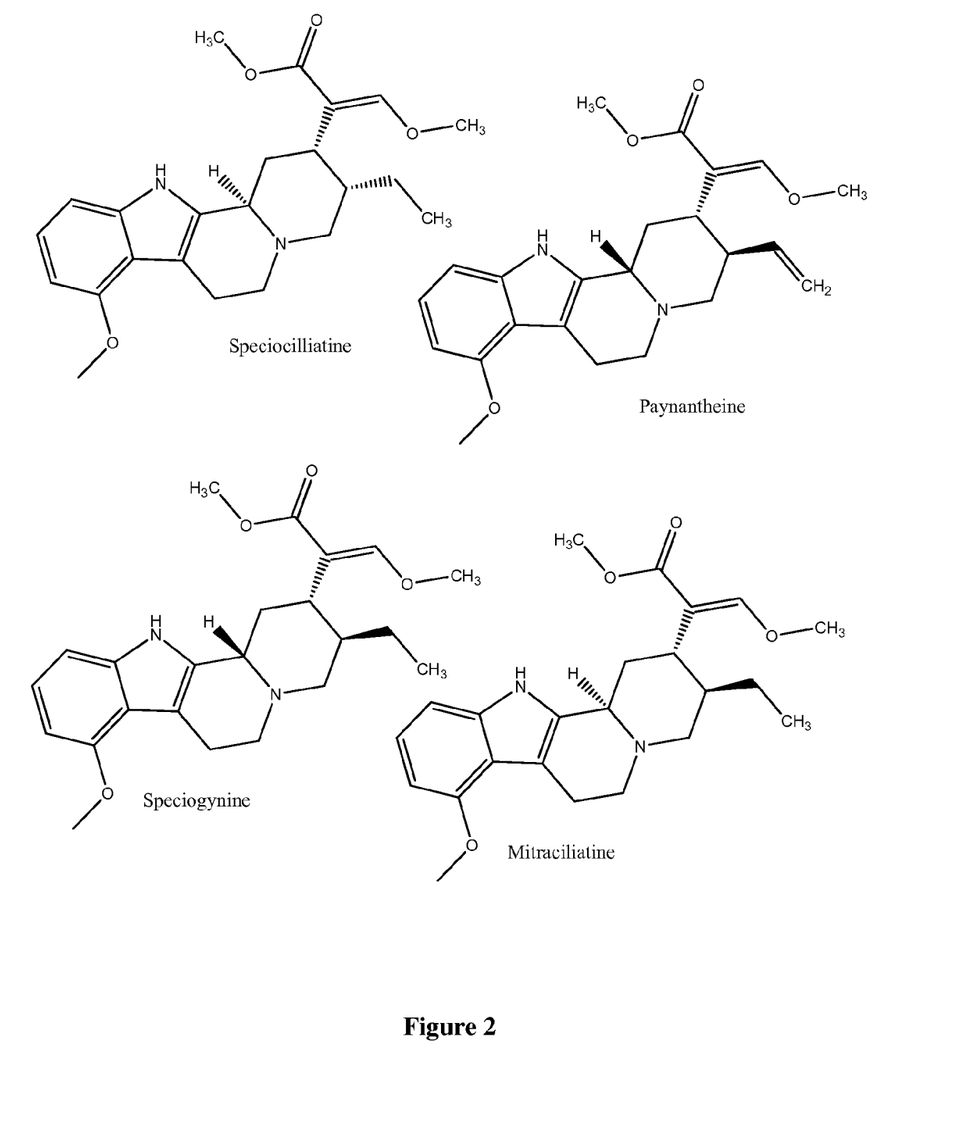
FIG. 2—Kratom alkaloids.
Figure 3:
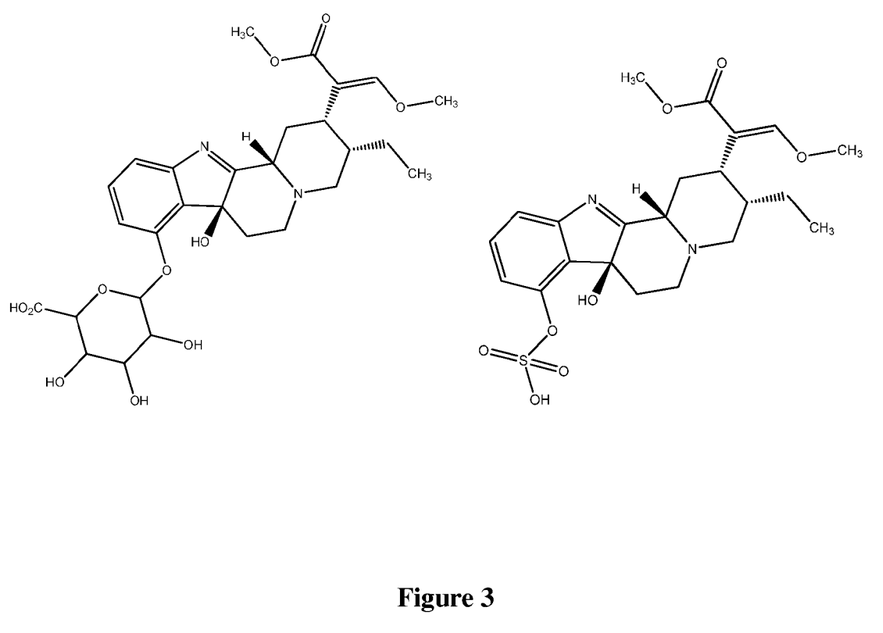
FIG. 3—Glucuronides and sulphates of 8-desmethylmitragynine.
Figure 4:
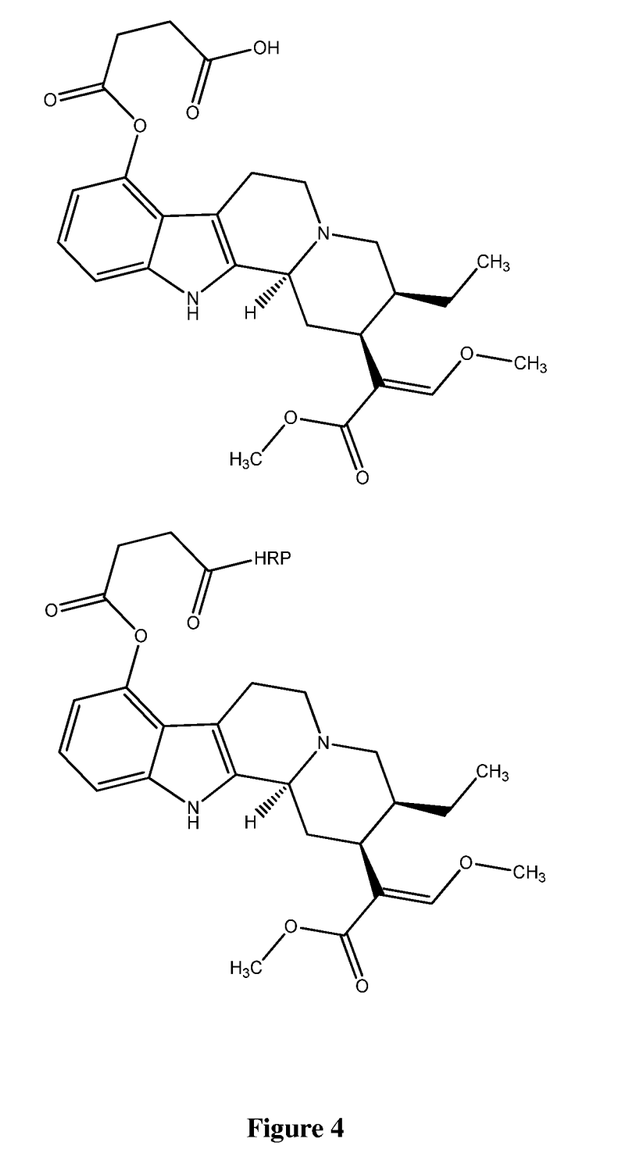

In a first aspect, the invention describes antibodies which bind specifically to an epitope of mitragynine and/or its respective metabolite, especially metabolites of mitragynine structurally altered at the 8-position such as 8-glucuronidyldmitragynine and 8-sulphonyldmitragynine. In a preferred embodiment the antibodies bind to mitragynine and the main metabolite 8-desmethylmitragynine (FIG. 1). 8-Desmethylmitragynine, 8-glucuronidyldmitragynine and 8-sulphonyldmitragynine metabolites correspond to mitragynine structurally altered at the 8-position. For example, for the metabolite 8-desmethymitragynine the structural alteration of mitragynine is the replacement of a methyl group by a hydrogen atom. The word 'specifically' implies that the antibodies of the invention almost exclusively bind to a molecular structure contained within and common to the aforementioned mitragynine molecules; this can be verified by calculating suitable metrics such as the sensitivity and cross-reactivity. The analyte with the greatest cross-reactivity is given a value of 100%, with all other analytes accorded a value relative to this. As recognised by the skilled person the antibody will also bind to other molecules to a certain extent; the important aspect for the validity of an immunoassay using the antibody is that the binding of the antibody to non-target molecules is at a relatively low level. The cross-reactivity of this extraneous binding by non-target molecules in the immunoassay incorporating the antibody is often less than about 1% and is frequently immeasurable. The antibody binds to mitragynine and has substantial cross-reactivity to 8-desmethylmitragynine. By substantial is meant at least 10%, preferably at least 30%, most preferably at least 50% cross-reactivity relative to mitragynine which is afforded a cross-reactivity value of 100%. The antibody also binds to other metabolites corresponding to mitragynine structurally altered at the 8-position. The skilled person would recognise that the similar structures of mitragynine and 8-desmethylmitragynine, the antibody of the invention highly likely recognising a common epitope, results in the antibody being able to sensitively bind to both molecules (as defined by a metric such as the $IC_{50}$).

In a further embodiment the antibodies are characterised by having been derived from an immunogen of Structure I Structure I

in which W is attached to the 8, 9, 10, or 11 position of the fused heterocyclic ring, and is N, O or S; X is -Q-Z—, in which Z, attached to W, is a crosslinking group selected from a $C_1$-$C_{10}$, preferably a $C_1$-$C_5$, substituted or unsubstituted straight or branched chain, saturated or unsaturated alkylene moiety and Q is, before conjugation to Y, a carboxylic acid or an ester thereof, an aldehyde, an amino group, a maleimide, a halocarboxylic acid or an ester thereof, a dithiopyridyl moiety, a vinylsulphone moiety, a thiocarboxylic acid or an ester thereof; Y is an antigenicity conferring carrier material which can be any macromolecule able to impart immunogenicity to the pre-immunogenic molecule but is preferably keyhole limpet haemocyanin (KLH), bovine serum albumin (BSA) or bovine thyroglobulin (BTG). Preferably the immunogen of Structure I has W═O and is Structure II

in which X and Y are as described previously. A preferred immunogen is Z═—$CH_2$—$CH_2$—CO—, Q=carboxylic acid and Y=BTG (see FIG. 3, top structure). The antibody is preferably specific to mitragynine and cross-reacts with its main metabolite 8-desmethylmitragynine.

The antibodies raised to the immunogen of Structure II can bind to other mitragynine analogues such as speciogynine, speciociliatine, paynantherine, and/or their various metabolites, including glucuronides and sulphates. The antibodies can be any suitable immunoglobulin-derived molecules (an 'antibody derivative') such as, but not limited to, a polyclonal, monoclonal, humanised, chimeric, short-chain or single chain variable fragments. The antibody is preferably a polyclonal or a monoclonal antibody. The antibodies of the invention can be adsorbed on or covalently attached to a substrate. The substrate can be any substance or shape to which an antibody or antibody derivative can bind, either through chemical bonds (before which the substrate has to be chemically activated) or passive adsorption through mutual attraction of the substrate and antibody. Preferably the antibodies are chemically bonded to the chemically activated substrate. The substrate can be for example plastic or magnetic beads, polystyrene microtitre plates (ELISA plates), planar nitrocellulose, a ceramic biochip or a biochip such as a plastic, glass or ceramic biochip surface-coated with a material that facilitates the immobilisation of the antibodies to the substrate. The antibodies or the substrate comprising the antibodies can be provided as discrete off-the-shelf reagents or be incorporated in a kit which optionally has other components such as a conjugate and/or calibrators.

In a second aspect the invention describes an immunoassay method of detecting or quantifying mitragynine, metabolites corresponding to mitragynine structurally altered at the 8-position and/or their corresponding metabolic glucuronides and sulphates in an in vitro sample taken from an individual, the method comprising contacting an in vitro sample taken from the individual with a conjugate and an antibody of the invention, detecting the bound conjugate, and deducing from a calibrator value or calibrator values the presence or amount of mitragynine, metabolites corresponding to mitragynine structurally altered at the 8-position and their corresponding metabolic glucuronides and sulphates. The conjugate preferably has the structure Structure III in which X is an organic spacing group and Y is a labelling agent which is detectable. X is Q-Z—, in which Z, attached to O, is a crosslinking group selected from a $C_1$-$C_{10}$, preferably a $C_1$-$C_5$, substituted or unsubstituted straight or branched chain, saturated or unsaturated alkylene moiety and Q is, before conjugation to Y, a carboxylic acid or an ester thereof, an aldehyde, an amino group, a maleimide, a halocarboxylic acid or an ester thereof, a dithiopyridyl moiety, a vinylsulphone moiety, a thiocarboxylic acid or an ester thereof; Y is any suitable labelling agent which can be selected from an enzyme, a luminescent substance, a radioactive substance, or a mixture thereof. Preferably, the labelling agent is an enzyme, preferably a peroxidase, most preferably horseradish peroxidase (HRP).

Particularly preferred groups for —X—Y are

Alternatively, or additionally, the luminescent substance may be a bioluminescent, chemiluminescent or fluorescent material. The conjugates of the method are made up of haptens attached to labelling agents. The haptens of the conjugates are molecules that can bind to the antibodies of the method. The use of haptens, conjugates and antibodies in the context of immunoassays is well known in the art. Besides mitragynine, the metabolite to be detected or quantified is 8-hydroxymitragynine; the corresponding glucuronidated and sulphated conjugates can also be detected or quantified. The skilled person would expect the various kratom stereoisomeric derivatives relating to hydrogen and ethyl group conformers at positions 3- and 12b- of mitragynine, namely speciogynine, speciociliatine and mitraciliatine, and their corresponding metabolites to be bound by the antibody of the invention, as well as the close structural analogue paynantheine. The individual's sample to be used for in vitro analysis can be any suitable biological tissue e.g. hair, but is preferably a biological fluid especially whole blood, serum, plasma or urine. The biological tissue or fluid may need preparation to render it suitable for analysis.

The antibody of the invention can be used in an immunoassay i) to detect or quantify the amount of mitragynine and/or its metabolites structurally altered at the 8-position in an in vitro sample taken from a patient or ii) to detect or quantify the amount of mitragynine in a substance suspected of incorporating mitragynine. It may be necessary to adapt the substance to a formulation appropriate for testing. For example, if the substance is an herbal mixture, an extraction step into a suitable liquid such as an organic solvent or water would have to be conducted prior to analysis by immunoassay. The detection and quantification criteria for an immunoassay platform includes, as is well-known in the art, exceeding a pre-defined cut-off/concentration value or measuring the calibrator equivalent value as derived from a calibrator curve (also referred to as a standard curve). The format of an immunoassay for detecting or quantifying mitragynine and its metabolites can be singleplex or multiplex; a singleplex immunoassay implies that only mitragynine and its metabolites can be detected, while a multiplex immunoassay implies that one or more analytes other than mitragynine and its metabolites can be detected. Generally, in a multiplex format, each analyte is detected by different antibodies, each antibody specific to an individual analyte or to structurally similar analytes (as in mitragynine and its metabolites).

A third aspect of the invention is a kit comprising an antibody of the invention. The kit may also include a conjugate, preferably a conjugate of Structure III.

Methods and Examples

General Methodology
Preparation of Haptens, Immunogens and Detecting Agents.

Although haptens provide defined structural epitopes, they are not in themselves immunogenic and therefore need to be conjugated to carrier materials, which will elicit an immunogenic response when administered to a host animal. Appropriate carrier materials commonly contain poly(amino acid) segments and include polypeptides, proteins and protein fragments. Illustrative examples of useful carrier materials are bovine serum albumin, egg ovalbumin, bovine gamma globulin, bovine thyroglobulin, keyhole limpet haemocyanin etc. Alternatively, synthetic poly(amino acids) having a sufficient number of available amino groups, such as lysine, may be employed, as may other synthetic or natural polymeric materials bearing reactive functional groups. Also, carbohydrates, yeasts or polysaccharides may be conjugated to the hapten to produce an immunogen. The haptens can also be coupled to a detectable labelling agent to form a conjugate. The detectable labelling agent can be an enzyme (for example, horseradish peroxidase), a substance having fluorescent properties or a radioactive label for the preparation of detecting agents for use in the immunoassays. The fluorescent substance may be, for example, a monovalent residue of fluorescein or a derivative thereof. Immunogen formation for the invention described herein involves conventional conjugation chemistry. In order to confirm that adequate conjugation of hapten to carrier material has been achieved, prior to immunisation, each immunogen is evaluated using matrix-assisted UV laser desorption/ionisation time-of-flight mass spectroscopy (MALDI-TOFMS).

General Procedure for MALDI-TOF Analysis of Immunogens.

MALDI-TOF mass spectrometry can be performed using a Voyager STR Biospectrometry Research Station laser-desorption mass spectrometer coupled with delayed extraction. An aliquot of each sample to be analysed can be diluted in 0.1% aqueous trifluoroacetic acid (TFA) to create 1 mg/ml sample solutions. Aliquots (1 µl) can be analysed using a matrix of sinapinic acid and bovine serum albumin (Fluka) as an external calibrant.

Preparation of Antisera.

In order to generate polyclonal antisera, an immunogen of the present invention can be mixed with Freund's adjuvant and the mixture injected into a host animal, such as rabbit, sheep, mouse, guinea pig or horse. Sheep are a preferred host animal. Further injections (boosts) can be made and serum is sampled for evaluation of the antibody titre. When the optimal titre has been attained, the host animal is bled to yield a suitable volume of specific antiserum. The degree of antibody purification required depends on the intended application. For many purposes, there is no requirement for purification, however, in other cases, such as where the antibody is to be immobilised on a solid support, purification steps can be taken to remove undesired material and eliminate non-specific binding.

Immunoassay Development.

The process of developing an immunoassay is well known to the person skilled in the art. Briefly, for a competitive immunoassay in which the target analyte is a non-immunogenic molecule such as a hapten, the following process can be conducted: a detecting agent (conjugate) is added to a sample containing the target analyte and the raised antibodies, and the detecting agent (conjugate) and analyte compete for binding to the antibodies. The process may comprise fixing the antibodies to a backing substrate such as a polystyrene solid support or a ceramic chip. The antibodies can be polyclonal or monoclonal obtained using standard techniques. The signal emitted in the immunoassay is proportionate to the amount of detecting agent bound to the antibodies which in turn is inversely proportionate to the analyte concentration. The signal can be detected or quantified by comparison with a calibrator.

EXAMPLES

Figure 5:
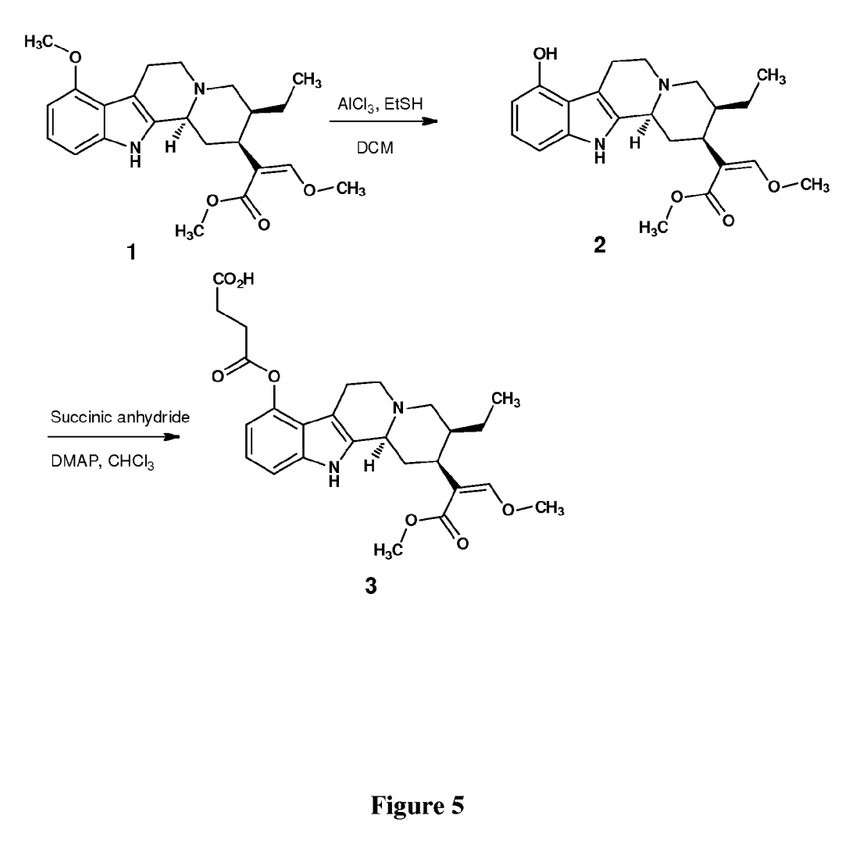
FIG. 5—Synthesis of 8-desmethylmitragynine hem isuccinate (Hapten 3).

Bold numbers in the following Examples correspond to the numbers of FIG. 5

Example 1: Preparation of 8-desmethylmitragynine 2

Mitragynine 1 (500 mg, 1.25 mmol) was dissolved in anhydrous dichloromethane (50 ml) and cooled at 0° C. Aluminum chloride (502 mg, 3.76 mmol) was added followed by the addition of ethanethiol (1.66 ml, 22.5 mmol) and the reaction mixture was stirred at 0° C. for 30 min and then at room temperature overnight. The solvents were evaporated in vacuo and the residue was purified by column chromatography (silica gel, 2% methanol in dichloromethane, 2 separations needed) to give 229 mg (48% yield) 8-desmethylmitragynine 2 as green brown oil.

Example 2: Preparation of 8-desmethylmitragynine Hemisuccinate 3

8-desmethylmitragynine 2 (65 mg, 0.169 mmol) was dissolved in anhydrous chloroform (10 ml) and succinic anhydride (74 mg, 0.742 mmol) was added at room temperature followed by the addition of dimethylaminopyridine (DMAP) (45 mg, 0.372 mmol). The reaction mixture was stirred overnight at room temperature. The reaction mixture was concentrated in vacuo to dryness and the residue was tritrated 2 times with ethyl acetate and 2 times with diethylether then dried under nitrogen to give 90 mg of 8-desmethylmitragynine hemisuccinate 3

Example 3: Conjugation of 8-desmethylmitragynine Hemisuccinate 3 to BSA

To a solution of 8-desmethylmitragynine_hemisuccinate 3 (18.4 mg, 0.038 mmol) in DMF (1.0 ml) was added N,N-dicyclohexylcarbodiimide (DCC) (8.53 mg, 0.041 mmol) and N-hydroxysuccinimide (4.76 mg, 0.041 mmol) and the mixture was stirred at room temperature overnight. The dicyclohexylurea formed was removed by filtration and the solution was added dropwise to a solution of BSA (50 mg, 1.5 µmol) in 50 mM sodium bicarbonate solution (pH 8.5) (5 ml). The mixture was then stirred overnight at 4° C. The solution was then dialysed against 50 mM phosphate buffer pH 7.2 (3 changes) for 24 hours at 4° C., and freeze-dried. MALDI results showed 23.66 molecule of 8-desmethylmitragynine hemisuccinate 3 had been conjugated to one molecule of BSA.

Example 4: Conjugation of 8-desmethylmitragynine Hemisuccinate 3 to BTG

To a solution of 8-desmethylmitragynine hemisuccinate 3 (65.4 mg, 0.135 mmol) in DMF (1.0 ml) was added N,N-dicyclohexylcarbodiimide (DCC) (33.4 mg, 0.162 mmol) and N-hydroxysuccinimide (18.64 mg, 0.162 mmol) and the mixture was stirred at room temperature overnight. The dicyclohexylurea formed was removed by filtration and the solution was added dropwise to a solution of BTG (150 mg) in 50 mM sodium bicarbonate solution (pH 8.5) (5 ml). The mixture was then stirred overnight at 4° C. The solution was then dialysed against 50 mM phosphate buffer pH 7.2 (3 changes) for 24 hours at 4° C., and freeze-dried.

Example 5: Conjugation of 8-desmethylmitragynine Hemisuccinate 3 to HRP

EDC hydrochloride (10 mg) was dissolved in water (0.5 ml) and immediately added to a solution of 8-desmethylmitragynine hemisuccinate 3 (2 mg) in DMF (0.2 ml). After mixing, this solution was added dropwise to a solution of HRP (20 mg) in water (1 ml). Sulfo-NHS (5 mg) was added and the reaction mixture was incubated in the dark at room temperature overnight. Excess hapten was removed with double PD-10 columns (Pharmacia) in series, pre-equilibrated with PBS at pH 7.2. The hapten-HRP conjugate was then dialysed overnight against PBS (101) at pH 7.2 at 4° C.

Example 6: Antibody Production

Immunogen (2 mg) was prepared in PBS, mixed at a ratio of 50% immunogen in PBS to 50% Freund's Complete adjuvant (Sigma, Product Number F5881) and emulsified by repeatedly passing the mixture through a tip on the end of a 1 ml syringe, until semi-solid. The emulsified mixture (1 ml) was injected intramuscularly into the sheep (the primary immunisation dose). Further injections (boosts) were prepared (1 mg of immunogen is prepared in PBS and mixed at a ratio of 50% immunogen in PBS/50% Freunds Incomplete Adjuvant, Sigma, Product Number—F5506) and injected (1 ml) intramuscularly at monthly intervals. Serum was sampled monthly by collection of whole blood from the jugular vein for evaluation of the antibody titre. Prior to immobilisation on a solid substrate (the biochip) the serum was purified using caprylic acid/ammonium sulphate precipitation.

Example 7: Mitragynine and 8-desmethylmitragynine Standard Curve Generation Using Generated Antiserum The HRP depleted IgG fraction of the antiserum was immobilized to the surface of a Randox biochip at a discrete test region by incubating for about 2 hrs at 37° C. (see EP0874242). A competitive chemiluminescent immunoassay was employed for the assay with mitragynine or 8-desmethylmitragynine in the specimen and hapten labeled with horseradish peroxidase (HRP). Increased levels of mitragynine or 8-desmethylmitragynine lead to reduced binding of hapten labeled with HRP and thus a reduction in the chemiluminescent signal emitted. The light signal generated from the test regions on the biochip was detected using digital imaging technology and compared to that from a calibration curve. The concentration of analyte present is calculated from the calibration curve. Mitragynine or 8-desmethylmitragynine was prepared in buffer base at 40 ng/ml and serially diluted 2-fold to give 8 additional levels of 20 ng/ml, 10 ng/ml, 5 ng/ml, 2.5 ng/ml, 1.25 ng/ml, 0.625 ng/ml, 0.313 ng/ml and a blank at 0 ng/ml. 25 µl of each standard was added to each well of the 9 well Biochip carrier with 155 µl of assay diluent. The hapten-labeled horseradish peroxidase (120 µl, Example 5) was then added to each well and incubated for 30 min at 30° C. at 370 rpm using a Randox Evidence Investigator thermoshaker. Following incubation, the liquid was decanted and the wells were washed with Evidence wash buffer, 6 quick washes and 6 two minute soaks were completed after which the liquid was decanted and the carrier tapped onto lint free paper. Luminol-EV841 & Peroxide (Randox Laboratories Ltd) were mixed (1:1) to give working strength signal reagent and 250 µl added to each well. The Biochip carrier was then incubated for 2 minutes protected from light and imaged using the Evidence Investigator camera. Results are shown in Table 1.

Results

TABLE 1

Biochip assay data employing antibodies of the invention
(antisera generated in response to the immunogen of Example 4)

| ng/ml | Mitragynine | | | 8-Desmethylmitragynine | | |
|---|---|---|---|---|---|---|
| | $A_{450}$ | % CV | B/Bo | $A_{450}$ | % CV | B/Bo |
| 0.000 | 1.612 | 4.1 | 100 | 1.510 | 1.0 | 100 |
| 0.313 | 1.216 | 6.4 | 75 | 1.116 | 6.0 | 74 |
| 0.625 | 1.012 | 6.3 | 63 | 0.956 | 4.6 | 63 |
| 1.250 | 0.787 | 7.2 | 49 | 0.816 | 2.7 | 54 |
| 2.500 | 0.590 | 10.9 | 37 | 0.633 | 3.7 | 42 |
| 5.000 | 0.401 | 10.1 | 25 | 0.441 | 1.4 | 29 |
| 10.000 | 0.273 | 7.5 | 17 | 0.279 | 3.2 | 18 |
| 20.000 | 0.177 | 13.1 | 11 | 0.191 | 2.4 | 13 |
| $IC_{50}$ (ng/ml) | | 1.193 | | | 1.532 | |
| % CR | | 100.00 | | | 77.87 | |

$A_{450}$ = absorbance at 450 nm;
B = absorbance at 450 nm at x ng/ml calibrator concentration;
$B_0$ = absorbance at 450 nm at 0 ng/ml calibrator concentration;
$IC_{50}$ = standard concentration which produces 50% B/$B_0$;
% CR = percentage cross-reactivity based on 100% specificity to mitragynine.

The invention claimed is:

1. A polyclonal antibody, which binds specifically to an epitope of one or more of mitragynine, 8-desmethylmitragynine, 8-sulphonylmitragynine, and 8-glucuronidylmitragynine;

wherein the polyclonal antibody has about 77.87% cross-reactivity to 8-desmethylmitragynine based on 100% cross-reactivity to mitragynine, wherein said cross-reactivity is measured in the presence of a conjugate having the structure wherein HRP is horseradish peroxidase.

2. The polyclonal antibody of claim 1, which binds specifically to an epitope of mitragynine and 8-desmethylmitragynine.

3. The polyclonal antibody of claim 1, wherein the antibody is produced using an immunogen having the structure:

wherein BTG is bovine thyroglobulin.

4. A method for detecting or quantifying one or more of mitragynine, 8-desmethylmitragynine, 8-sulphonylmitragynine, and 8-glucuronidylmitragynine in a sample, the method comprising:

(i) providing a mixture of the sample, the polyclonal antibody of claim 1 and a conjugate having the structure:

wherein HRP is horseradish peroxidase;
(ii) allowing the polyclonal antibody to bind to the conjugate and one or more of mitragynine, 8-desmethylmitragynine, 8-sulphonylmitragynine, and 8-glucuronidylmitragynine present in the sample;
(ii) detecting the presence of, or measuring the amount of, the conjugate bound to the polyclonal antibody, the presence or amount of the conjugate indicating the presence or amount of one or more of mitragynine, 8-desmethylmitragynine, 8-sulphonylmitragynine, and 8-glucuronidylmitragynine.

5. The method of claim 4, which detects or quantifies mitragynine and 8-desmethylmitragynine.

6. The method of claim 4, in which the sample is an in vitro human sample.

7. A kit comprising the polyclonal antibody according to claim 1 and a conjugate having the structure:

wherein HRP is horseradish peroxidase.

8. The method of claim 6, wherein the in vitro human sample is blood, plasma, serum, or urine.

* * * * *